(12) United States Patent
Mussivand (10) Patent No.: US 9,023,614 B2
(45) Date of Patent: May 5, 2015

(54) METHOD FOR COLLECTING CELLS FOR MACROMOLECULAR ANALYSIS

(76) Inventor: Tofy Mussivand, Navan (CA)

( * ) Notice: Subject to any disclaimer, the term of this patent is extended or adjusted under 35 U.S.C. 154(b) by 2338 days.

(21) Appl. No.: 10/887,352

(22) Filed: Jul. 9, 2004

(65) Prior Publication Data

US 2006/0008903 A1   Jan. 12, 2006

(51) Int. Cl.
| | |
|---|---|
| *C12N 5/00* | (2006.01) |
| *C12N 5/02* | (2006.01) |
| *C12N 13/00* | (2006.01) |
| *G01N 1/30* | (2006.01) |
| *G01N 33/48* | (2006.01) |
| *G01N 1/02* | (2006.01) |
| *G01N 1/40* | (2006.01) |
| *G01N 1/00* | (2006.01) |
| *G01N 30/00* | (2006.01) |

(52) U.S. Cl.
CPC ........ *G01N 1/02* (2013.01); *G01N 1/405* (2013.01); *G01N 2001/007* (2013.01); *G01N 2001/028* (2013.01); *G01N 2001/4094* (2013.01); *G01N 2030/009* (2013.01); *Y10S 435/97* (2013.01)

(58) Field of Classification Search
CPC ...... A61B 5/0002; A61B 5/0456; A61B 8/06; A61B 8/08; A61B 8/4472; A61B 8/543; G01N 1/02; G01N 1/405; G01N 2001/007; G01N 2001/028; G01N 2001/4094; G01N 2030/009
See application file for complete search history.

(56) References Cited

U.S. PATENT DOCUMENTS

| | | | | |
|---|---|---|---|---|
| 4,524,104 | A | 6/1985 | Hagio | 428/341 |
| 4,720,416 | A | 1/1988 | Duncan | 428/195 |
| 5,211,286 | A | 5/1993 | Turner | 206/223 |
| 5,364,759 | A | 11/1994 | Caskey et al. | 435/6 |
| 5,646,039 | A | 7/1997 | Northrup et al. | 435/287 |
| 5,856,102 | A | 1/1999 | Bierke-Nelson et al. | 435/6 |
| 5,879,939 | A | 3/1999 | Gray et al. | 435/379 |
| 5,891,694 | A * | 4/1999 | Arisawa et al. | 435/173.7 |
| 5,989,431 | A | 11/1999 | Evans et al. | 210/645 |
| 6,168,922 | B1 | 1/2001 | Harvey et al. | 435/6 |
| 6,316,248 | B1 | 11/2001 | Elliott et al. | 435/270 |
| 6,355,439 | B1 | 3/2002 | Chung et al. | 435/6 |
| 6,489,164 | B1 | 12/2002 | Gray et al. | 435/378 |
| 6,503,716 | B1 | 1/2003 | Lai et al. | 435/6 |
| 6,607,699 | B1 | 8/2003 | Elliott et al. | 422/61 |

FOREIGN PATENT DOCUMENTS

WO    WO 01/36959    5/2001   ............ G01N 29/02

OTHER PUBLICATIONS

An Efficient Method for the Extraction of DNA for Formalin Fixed, Paraffin Embedded Tissue by Sonication: M.J. Heller, L.J. Burgart, C.J. Ten Eyck, M.E. Anderson, T.C. Greiner, R.A. Robinson; Biotechniques, 11, #3, 1991, pp. 372-377.
"DNA Fingerprinting from Fingerprinting"; Van Oorchot RA, Jones MK; Nature 1997;378(6635);767.
"Fingerprints and DNA: STR Typing of DNA Extracted From Adhesive Tape After Processing for Fingerprints"; Zamir A., Springer E., Glattsten B.; Journal of Forensic Sciences 2000, 45(3): 687-688.
Afghani B and Stutman HR. Polymerase chain reaction for diagnosis of *M. tuberculosis*: Comparison of simple boiling and a conventional method for DNA extraction. Biochemical and Molecular Medicine 1996; 57: 14-18.
Akane A, Matsubara K, et al. Identification of the heme compound copurified with deoxyribonucleic acid (DNA) from bloodstains, a major inhibitor of polymerase chain reaction (PCT) amplification. Journal of Forensic Sciences 1994; 39(2): 362-372.
Anderson KL and Lebepe-Mazur S. Comparison of rapid methods for the extraction of bacterial DNA from colonic and caecal lumen contents of the pig. Journal of Applied Microbiology 2003; 94: 988-993.
Anderson TD, Ross JP, et al. A validation study for the extraction and analysis of DNA from human nail material and its application to forensic casework. Journal of Forensic Sciences 1999; 44(5): 1053-1056.
Bolano A, Stinchi S, et al. Rapid methods to extract DNA and RNA from cryptococcus neoformans. FEMS Yeast Research 2001; 1: 221-224.
Bourke M. Scherczinger CA, et al. NaOH treatment to neutralize inhibitors of taq polymerase. Journal of Forensic Sciences 1999; 44(5): 1046-1050.
Casas I, Powell L, et al. New method for the extraction of viral RNA and DNA from cerebrospinal fluid for use in the polymerase chain reaction assay. Journal of Virological Methods 1995; 53: 25-36.
Cattaneo C, Craig OE, et al. Comparison of three DNA extraction methods on bone and blood stains up to 43 years old and amplification of three different gene sequences. Journal of Forensic Sciences 1997; 42(6): 1126-1135.
Chung Y., Hwang C. Kim E. Palm print as a replacement of blood-drawing for DNA tests. Tenth International Symposium on Human Identification 1999, 8p.
Cline RE, Laurent NM, et al. The fingernails of Mary Sullivan : Developjing reliable methods for selectively isolating endogenous and exogenous DNA from evidence. Journal of Forensic Sciences 2003; 48(2): 328-333.
Comey CT, Koons BW, et al. DNA extraction strategies for amplified fragment length polymorphism analysis. Journal of Forensic Sciences 1994; 39(5):1254-1269.

(Continued)

*Primary Examiner* — Debbie K Ware
(74) *Attorney, Agent, or Firm* — Norton Rose Fulbright Canada LLP (57) ABSTRACT

A method for rapidly collecting cells from a surface, such as a surface bearing fingerprints, for subsequent macromolecular analysis involves dispensing a predetermined amount of an aqueous solution onto the surface, and subjecting the aqueous solution to ultrasound waves to promote a detachment of the cells from the surface. Extraction of macromolecules such as DNA from the cells can be effected directly in the solution containing the collected cells by further subjecting the solution to ultrasound waves for a prescribed period of time to lyse the cells, and then extracting the DNA.

25 Claims, 5 Drawing Sheets

(56) References Cited

OTHER PUBLICATIONS

Drabkova L, Kirschner J, et al. Comparison of seven DNA extraction and amplification protocols in historical herbarium specimens of juncaceae. Plant Molecular Biology Reporter 2002; 20: 161-175.

Gangitano DA, Garofalo MG, et al. Typing of the lcus DYS19 from DNA derived from fingernail clippings using PCR Concert™ rapid purification system. Journal of Forensic Sciences 2002; 47(1): 175-177.

Giraffa G, Rossetti L, et al. An evaluation of chelex-based DNA purification protocols for the typing of lactic acid bacteria. Journal of Microbiological Methods 2000; 42: 175-184.

Gustincich S, Manfioletti G, Del Sal J, et al. A fast method for high-quality genomic DNA extraction from hole human blood. Biotechniques 1991; 11(3): 298-300, 302.

Hoff-Olsen P, Mevag B, et al. Extraction of DNA from decomposed human tissue: An evaluation of five extraction methods for short tandem repeat typing. Forensic Science International 1999; 105: 171-183.

Joshi CG, Rank DN, et al. Comparion of DNA extraction protocols in frozen stored blood samples. Indian Veterinary Journal 1998; 75: 1038-1039.

Klintschar M and Neuhuber F. Evaluation of an alkaline lysis method for the extraction of DNA from whole blood and forensic stains for STR analysis. Journal of Forensic Sciences 2000; 45(3): 669-673.

Konomi N, Lebwohl E. et al. Comparison of DNA and RNA extraction methods for mummified tissues. Molecular and Cellular Probes 2002; 16: 445-451.

Larkin A and Harbison SA. An improved method for STR analysis of bloodstained denim. International Journal of Legal Medicine 1999; 112: 388-390.

Lederer T, Betz P, et al. DNA analysis of fingernail debris using different multiplex systems: a case report. International Journal of Legal Medicine 2001; 114: 263-266.

Lee YK, Kim HW, et al. A simple method for DNA extraction from marine bacteria that produce extracellular materials. Journal of Microbiological methods 2003; 52: 245-250.

Lorent M, Entrala C, et al. Dandruff as a potential source of DNA in forensic casework. Journal of Forensic Sciences 1998; 43(4): 901-902.

Oberbauer AM, Grossman DI, et al. Alternatives to blood as a source of DNA for large-scale scanning studies of canine genome linkages. Veterinary Research Communications 2003; 27: 27-38.

Oz C and Zamir A. An evaluation of the relevance of routine DNA typing of fingernail clippings for forensic casework. Journal of Forensic Sciences 2000; 45(1): 158-160.

Ricci U and Uzielli MLG. Fingernail, as an alternative source of DNA for forensic investigations and medical diagnostics: A new technique to obtain template DNA in critical situations. Acta Geneticae Medicae et Gemellologiae 1996; 45: 301-302.

Scherczinger CA, Bourke MT, Ladd C, et al. DNA extraction from liquid blood using QIAamp. J Forensic Sci 1997; 42(50): 893-896.

Tahir MA, Balraj E, et al. DNA typing of samples for polymarker, DQA1, and nine STR loci from a human body exhumed after 27 years. Journal of Forensic Sciences 2000; 45(4): 902-907.

Tahir MA and Watson N. Typing of DNA HLA-DQα alleles extracted from human nail material using polymerase chain reaction. Journal of Forensic Sciences 1995; 40(4): 634-636.

Teimer, Gunter et al., Isolation and physicochemical characterization of the DNA from normal human skin and psoriatic scale, Arch. Dem Res., 1976, 256: 241-246.

Van Hofstat DE, Deforce DL, Hubert De Pauw IP, et al. DNA typing of fingerprints using capillary electrophoresis; effect of dactyloscopic powders. Electrophoresis 1999; 20(14): 2870-2876.

Van Burik JA, Schreckhise RW, et al. Comparison of six extraction techniques for isolation of DNA from filamentous fungi. Medical Mycology 1998; 36:299-303.

Van Oorchot RA, Jones MK. DNA fingerprinting from fingerprints. Nature 1997; 378(6635): 767.

Vanderberg N, Van Oorschot Rah, et al. An evaluation of selected DNA extraction strategies for short tandem repeat typing. Electrophoresis 1997; 18: 1624-1626.

Vigilant L. An evaluation of techniques for the extraction and amplification of DNA from naturally shed hairs. Biological Chemistry 1999; 380: 1329-1331.

Vignoli C, de Lamballerie X, et al. Advantage of a rapid extraction method of HIV1 DNA suitable for polymerase chain reaction. Research in Virology 1995; 146: 159-162.

Walsh PS, Metzger DA, Higuchi R. Chelex 100 as a medium for simple extraction of DNA for PCR-based typing from forensic material. Biotechniques 1991; 10(4): 506-513.

Wang W, Kumar P, et al. PCR amplification of 40 year-old paraffin-embedded tumour tissues: Comparison of four different DNA extraction and purification methods. International Journal of Oncology 1994; 5:453-457.

Wiegand P, Bajanowski T, et al. DNA typing of debris from fingernails. International Journal of Legal Medicine 1993; 106: 81-83.

Yamada Y, Makimura K, et al. Comparison of different methods of extraction of mitochondrial DNA from human pathogenic yeasts. Japanese Journal of Infectious Diseases 2002; 55: 122-125.

Zamir A, Springer E. Glattsten B. Fingerprints and DNA; STR typing of DNA extracted from adhesive tape after processing for fingerprints. J of Forensic Sciences 2000, 45(3): 687-688.

* cited by examiner

METHOD FOR COLLECTING CELLS FOR MACROMOLECULAR ANALYSIS

CROSS-REFERENCE TO RELATED APPLICATIONS

This is the first application filed for the present invention.

TECHNICAL FIELD

The present invention relates to methods for collecting cells from surfaces and extracting macromolecules for molecular analysis, including deoxyribonucleic acid (DNA) from fingerprints.

BACKGROUND OF THE INVENTION

Genetic information is very important for many reasons including understanding life processes in biological systems, production and function of enzymes, hormones and neurotransmitters secretion and control of cellular functions. Furthermore, deoxyribonucleic acid (DNA) and other macromolecules can provide a wealth of information for disease diagnosis and prevention, forensic analysis and security through identification of individuals. DNA may also serve as a target for disease treatment.

However, methods for obtaining and extracting DNA are invasive, costly, laborious and time consuming. Typically, blood samples are obtained and shipped to laboratories for analysis. Drawing blood or obtaining material from other invasive sources such as tissue samples requires a licensed physician or nurse, or a trained technician. Moreover, there is discomfort associated with blood and other invasive means of collection as well as risk of disease transmission. Furthermore, blood and tissue samples are often not available from crime scenes for forensic analysis.

Current methods for collection and extraction of DNA involve many steps. Apart from being expensive and time consuming, each additional step may increase the risk of contamination, which can contribute to a degradation of the sample and therefore result in a loss of information.

DNA recovery is not limited to blood cells but may be obtained from less invasive sources such as from skin cells. For example, skin cells in fingerprints constitute valuable material in forensic analysis. However, existing methods for performing DNA analysis from skin cells left on surfaces are, as mentioned above, time consuming and often do not provide a sufficient amount of material to enable a routine and reliable DNA extraction.

An improved method for collecting and extracting macromolecules such as DNA is therefore needed.

SUMMARY OF THE INVENTION

It is therefore an object of the invention to provide an improved method for collecting cells from a surface and/or other sources for macromolecular analysis.

It is further an object of the invention to provide a method for collecting DNA from a surface by collecting the cells and isolating the DNA from the cells, including fingerprints.

In one embodiment, the present invention provides a method for rapidly and efficiently collecting cells from a surface, with a minimum of steps, for macromolecular analysis. The method uses ultrasonic energy to promote the detachment of cells from the surface. The method further allows for a rapid collection of the cells directly from the surface into an aqueous solution that is readily amenable to macromolecular analysis such as DNA analysis. The cells can be efficiently collected from different types of surfaces which include but are not limited to glass, plastic, hair and nail clippings.

In an aspect of the method, macromolecular extraction, such as DNA extraction, can be performed directly in the aqueous solution containing the collected cells thereby substantially reducing the number of steps involved in the processing the sample and the risk of contamination.

In yet another aspect of the method the aqueous solution may contain a proteinase to expedite DNA extraction and/or to facilitate the collections of cells that may be adhered to a surface by cell surface proteins.

BRIEF DESCRIPTION OF THE DRAWINGS

Further features and advantages of the present invention will become apparent from the following detailed description, taken in combination with the appended drawings, in which:

FIG. 3a is a schematic illustration of principal steps in DNA extraction using cells collected from a surface in accordance with the method shown in FIG. 2a; and FIG. 3b is a schematic illustration of principal steps in macromolecule extraction using cells collected from a surface in accordance with the method shown in FIG. 2a.

It will be noted that throughout the appended drawings, like features are identified by like reference numerals.

DETAILED DESCRIPTION OF THE PREFERRED EMBODIMENT

The invention provides a method for collecting cells from a surface to enable macromolecular analysis, and for isolating macromolecules from collected cells. Advantageously, the isolation of macromolecules, such as DNA, can be performed quickly and on site.

While it has long been known that only a very small amount of DNA (0.1-10 nanograms) is required for analysis of specific sequences to identify a person, for example, the practice of using fingerprints, palm prints, footprints, or other skin contact traces, and other non-invasive traces of a person to extract DNA has not, to date, proved practical.

Figure 1:
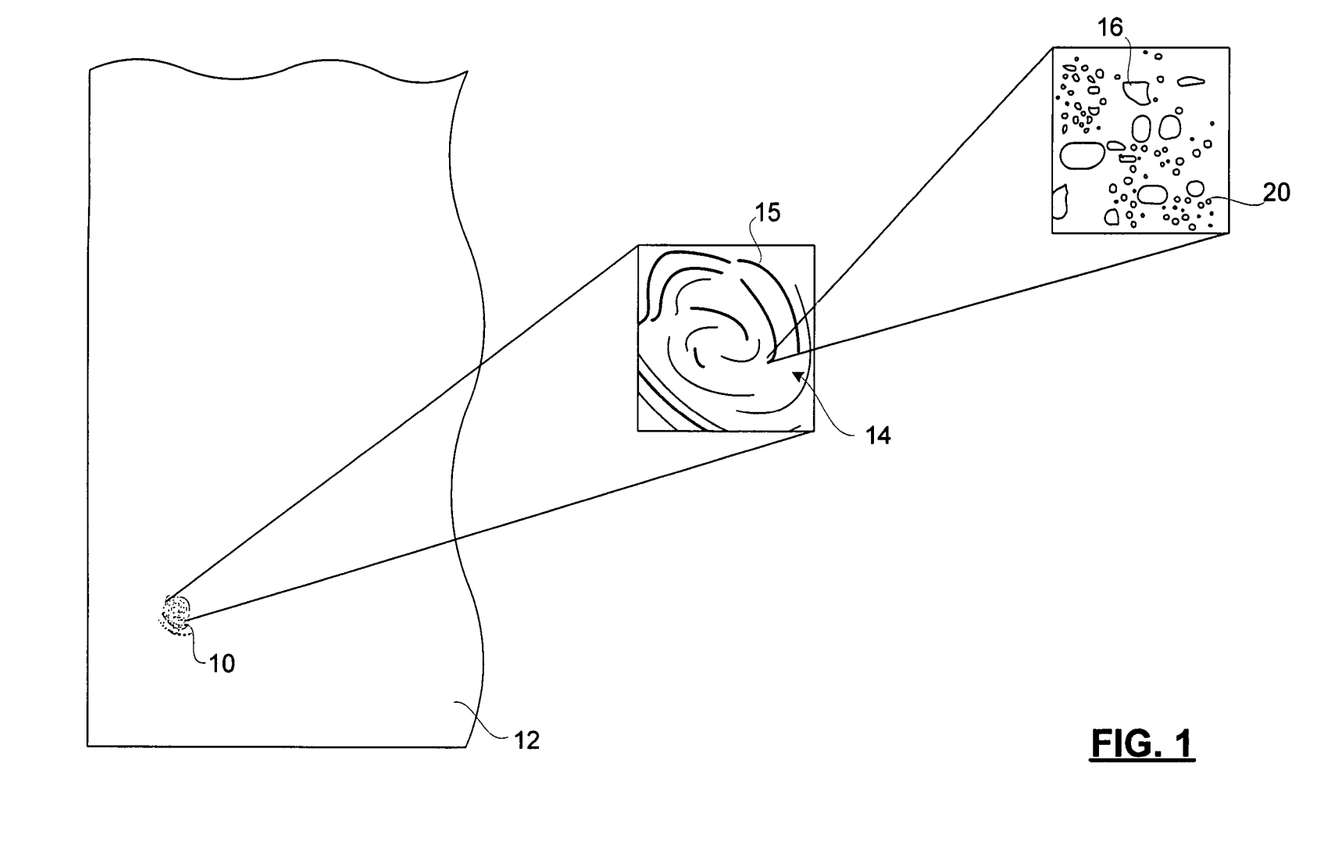
FIG. 1 is a schematic illustration of a fingerprint at three magnifications.

FIG. 1 schematically illustrates a fingerprint 10 on a surface 12. At roughly 4 times enlargement, a biometric pattern 14 of grooves 15 (characterized primarily by arches, loops, and whorls) can be readily discerned. Such patterns have been extensively used for forensic identification for many years. At roughly 20 times magnification, a volume of dirt, and debris 16 of different kinds may be evident. Tests have shown that this residual matter typically includes a sufficient density of shed skin cells 20 to permit DNA or other macromolecule identification using a method described in detail below.

It should be noted that the surface 12 may be a substantially immobile object, or may be a tape or other transportable medium onto which the fingerprint 10 was transferred from another surface. For example, it is well known in the forensic sciences to lift a fingerprint from a surface by contacting it with a piece of plastic tape designed for that purpose. It has been found that the present invention may be practiced with a sample collected using a piece of tape or like medium onto which the fingerprint has been transferred, and further can be applied to such a fingerprint transferred to another medium at least one year earlier, as is documented below with experimental evidence.

Figure 2A:
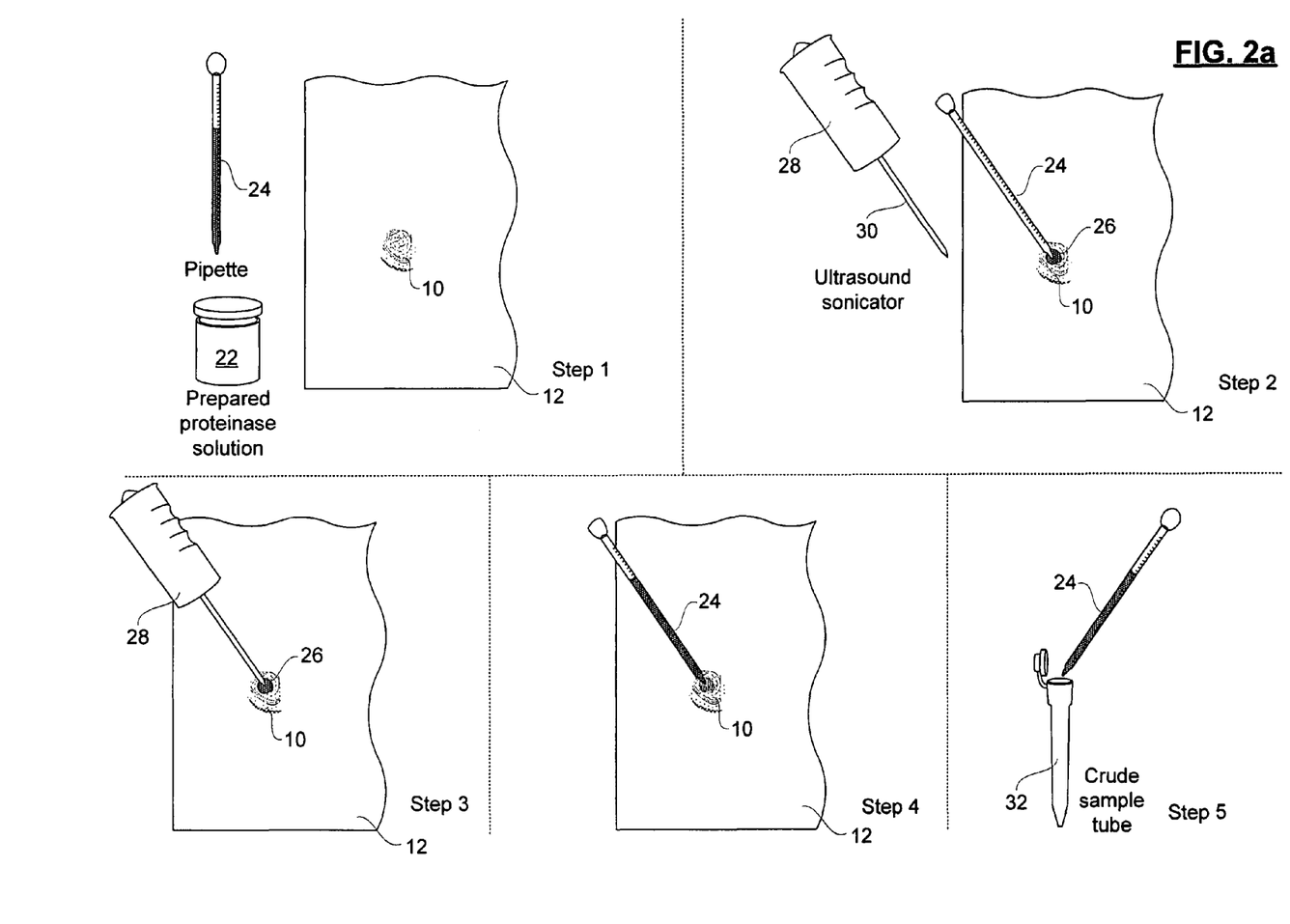
FIG. 2a is a schematic illustration of principal steps in collecting cells from a surface bearing a fingerprint.

FIG. 2a schematically illustrates principal steps in a method for collecting cells from the fingerprint 10 on the surface 12, in accordance with an embodiment of the invention. A first step involves applying a predefined volume of an aqueous solution 22, such as a prepared proteinase solution, to the surface 12 over the fingerprint 10. If DNA is to be extracted from the collected cells, a proteinase may be included in the solution to facilitate the extraction steps. The proteinase may also be useful for promoting detachment of the cells from the surface in cases where the adherence of cells 20 to the surface 12 is promoted by protein attachment (which may be especially strong if the surface 12 is plastic or glass). For example, a dilution of Trypsin (commercially available from Invitrogen of Carlsbad, Calif.), in an aqueous buffer, for example Hanks balanced salt solution (BSS) (commercially available from Cambrex Bioproducts) may be used. Balanced salt solutions containing Trypsin are well known in the art of laboratory cell culture analysis, and will not be further described herein.

In accordance with the illustrated embodiment, a pipette 24 is used for dispensing the predetermined volume of the aqueous solution 22. It is contemplated that the aqueous solution 22 may be supplied in a single use sachet or other container such as an Eppendorf™ tube that permits a controlled dispensation of a predetermined volume of the aqueous solution 22. In step 2, the aqueous solution 22 is taken up into the pipette 24, and in step 1 is applied to the fingerprint 10, leaving a droplet 26 of the aqueous solution 22 on the fingerprint 12.

To facilitate extraction and isolation of the macromolecule (hereinafter presumed to be DNA) and to ensure that a sufficient concentration of DNA is procured, it is preferable to control a volume of the aqueous solution 22 that is dispensed onto the surface 12. For example, 0.1-0.15 milliliters of the aqueous solution 22 is an acceptable volume for this purpose.

In step 3, an ultrasound sonicator 28 is used to agitate the droplet 26 to liberate the cells 20 from the surface 12. A sonotrode 30 of the sonicator 28 is placed on the droplet 26. Care is taken not to permit the tip of the sonotrode 30 to contact any surface that might impart contaminants, such as a DNAse for example, to the sample within the droplet 26.

The sonicator 28 is actuated to apply an ultrasonic wave to the droplet 26 according to a prescribed regimen. For example, an ultrasonic wave with a frequency of 30 kilohertz may be applied for 1-2 minutes. In an embodiment in which a droplet of about 0.1 to 0.15 milliliters has been deposited on the surface, a sonotrode with a 0.5 millimeter (mm) diameter tip may be used, and a power density of 125 Watts/cm$^2$, has been found sufficient for releasing substantially all cells 20 from typical fingerprint-bearing surfaces. The diameter of the tip of the sonotrode may be selected as a function of the volume of the droplet with smaller volumes requiring smaller diameter such that the tip can be inserted in the droplet to ensure propagation of the ultrasound waves within the droplet. Manual dexterity of the user is required to support the sonotrode 30 in contact with the droplet for the duration of the initial sonication, unless a mechanical support is used. Of course the duration of the sonication may be extended or reduced depending on the affinity of the proteins for the surface, and the amount of proteinase used, etc.

It will be appreciated that the ultrasound alone may be sufficient to promote detachment of the cells from the surface. Consequently, it is not always necessary to include a proteinase in the aqueous solution 22 for removal of the cells from the surface.

After the application of the sonicator 28, the sample-bearing droplet 26 which contains debris 16 and cells 20, is collected in step 4. As shown, the pipette 24 is used to collect the sample-bearing solution. Naturally, care has been taken not to contaminate the pipette 24. The sample-bearing droplet 26 of aqueous solution 22 is then placed into a crude sample tube 32 in step 5. In some embodiments, the means for collecting the sample-bearing droplet 26 could be different, including a suction tube coupled to the crude sample tube 32. Preferably the crude sample tube 32 is easy to handle and to seal, such as an Eppendorf® tube.

Figure 2B:
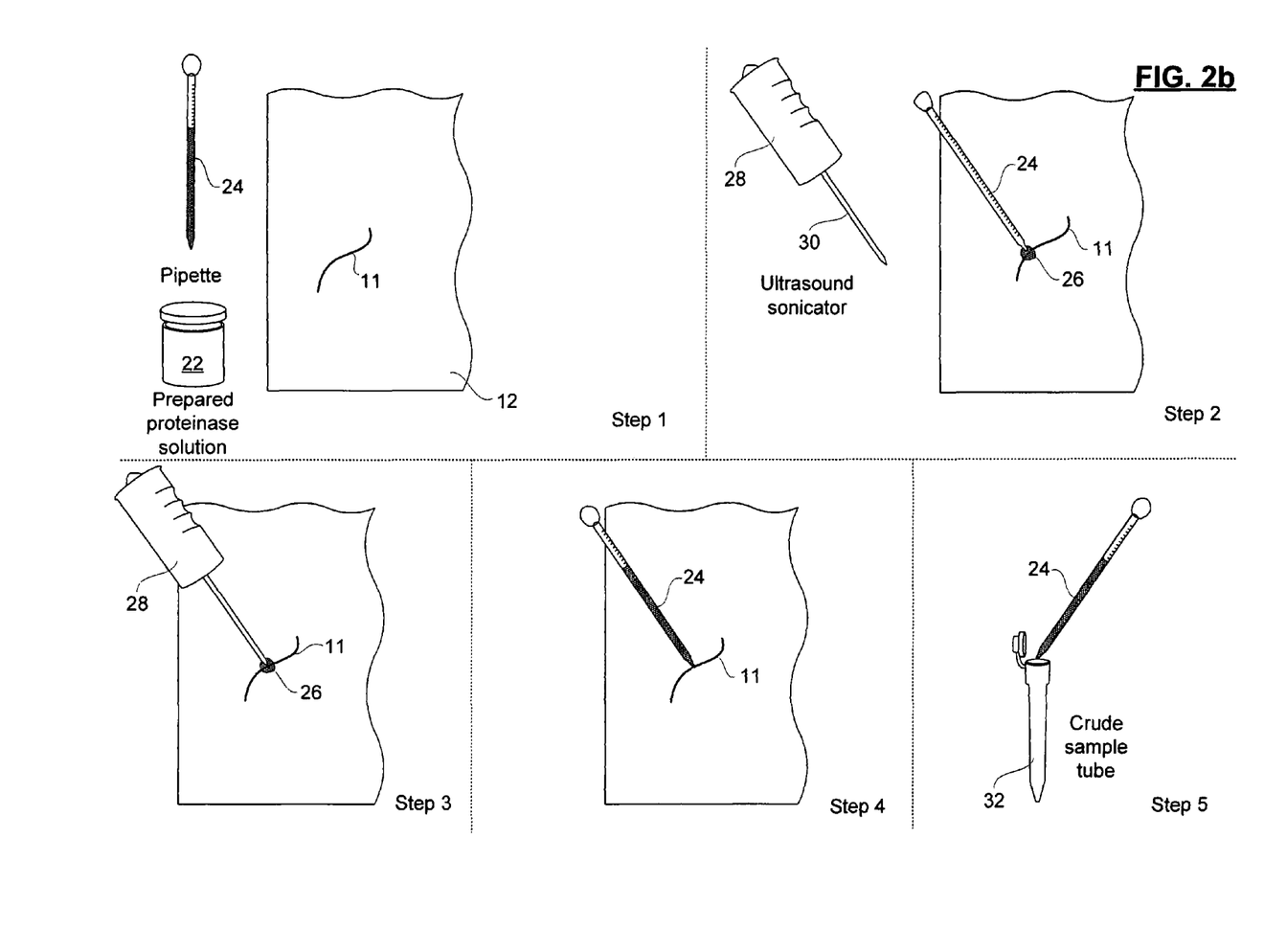
FIG. 2b is a schematic illustration of principal steps in collecting cells from a surface supporting a hair.

FIG. 2b schematically illustrates principal steps involved in a method for collecting cells from a hair 11 on the surface 12. It will be appreciated by those skilled in the art that there are several surfaces on which one would expect to find various skin cells, including hair and nail clippings, eyewear and jewelry, hand tools, and other surfaces that contact a part of a body. It should be noted that surfaces that provide an insubstantial fingerprint may provide adequate cell samples for DNA analysis, if the cells are collected using the method in accordance with the present invention.

Steps 1-5 of FIG. 2b are essentially identical to those of FIG. 2a. The method only differs in that the cells are recovered from a surface of a hair instead of a fingerprint.

Figure 3A:
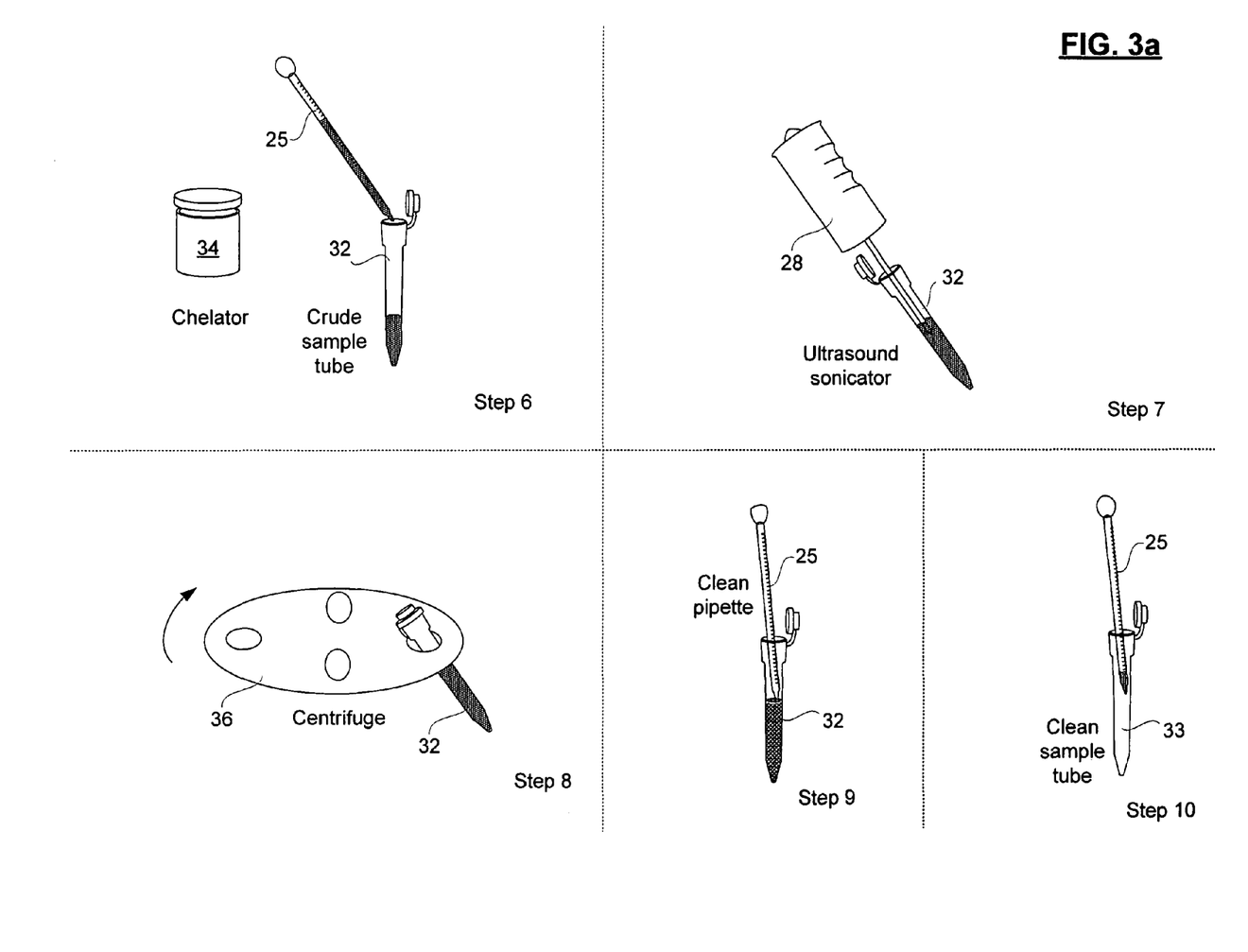

FIGS. 3a, b are schematic illustrations of principal steps involved in extracting DNA from a sample collected in accordance with the method shown in FIG. 2a or 2b. In accordance with the DNA extraction method shown in FIG. 3a, in step 6, a sample in the crude sample tube 32 is exposed to a chelator, such as Chelex-100 commercially available from Bio Rad Laboratories. A volume of about 0.15 ml of the Chelex solution is added to the sample using a clean pipette 25, and, in step 7, the sample is sonicated for an extended period of time to lyse the cells.

In step 8, the lysed content of the crude sample tube 32 is placed in a micro-centrifuge 36. The sample is centrifuged to filter and separate the DNA from a remainder of the sample. For example, subjecting the content of the crude sample tube 32 to 12,000 rpm for 3 minutes may be sufficient.

In steps 9 and 10 the supernatant of the content of the crude sample tube 32 is removed to a clean sample tube 33 using the pipette 25. The supernatant is purified DNA, which is recovered for analysis.

Figure 3B:
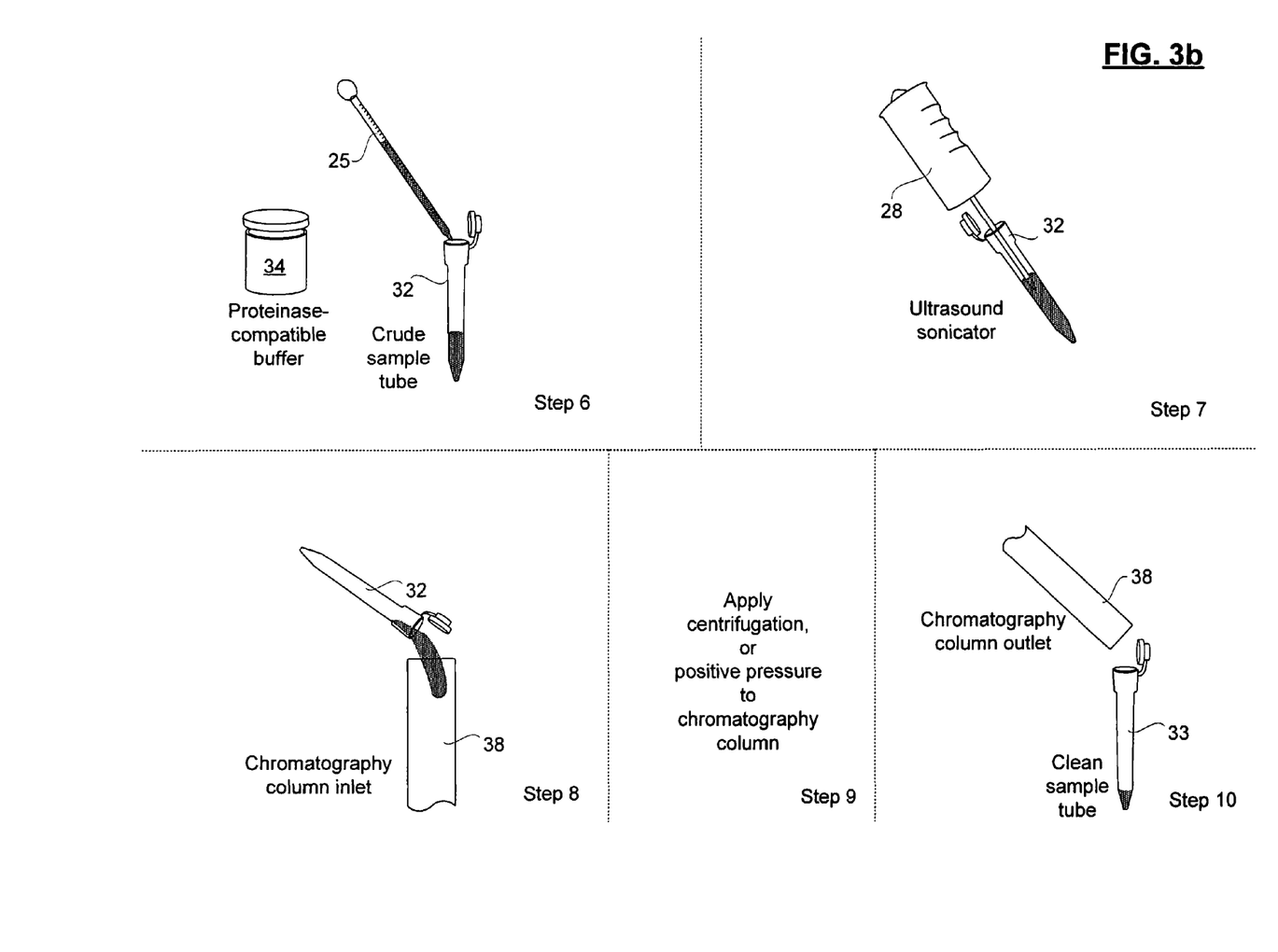

DNA extraction in accordance with the method shown in FIG. 3b, follows the same steps 6, and 7 as per the method described above with reference to FIG. 3a. However, the lysed content of the crude sample tube 32 is poured into (an inlet of) a chromatography column 38, in step 8 (instead of being centrifuged). Commercially available chromatography columns include those sold under the trade names Sephadex™ (by Amersham Biosciences) and Sephacryl™ (by Mobitec). To expedite filtration through the chromatography column 38, in step 9, the sample is either subjected to a positive pressure (for example on the order of 5 pounds per square inch), or to centrifugation for a period of 3-5 minutes. In either case, the purified DNA is collected from (an outlet of) the chromatography column 38, and is transferred to the clean sample tube 35.

It will be appreciated that different volumes of the proteinase solution 22 can be applied onto the surface depending on, for example, a porosity of the collection surface. Furthermore the content of the solution may depend on an affinity of the proteins on a surface of the cells 20 for the collection surface, and the surface area of the skin contact trace, or other types of cells that can be recovered non-invasively.

EXAMPLES

In order to verify the cell collection technique, and to determine compatibility with the identified DNA extraction methods, four sets of experiments were conducted.

Experiment 1

Efficacy of Cell Removal

The purpose of this experiment was to collect fingerprint samples left on a surface using the method for collection in accordance with the invention.

In forensic science, fingerprints are generally collected using either a swabbing method (Van Oorchot R A, Jones M K. *DNA fingerprinting from fingerprints. Nature* 1997; 378 (6635): 767.) or an adhesive tape method (Zamir A, Springer E, Glattsten B. *Fingerprints and DNA: STR typing of DNA extracted from adhesive tape after processing for fingerprints. Journal of Forensic Sciences* 2000, 45(3): 687-68; U.S. Pat. No. 6,355,439).

As described above, the sampling technique in accordance with the invention collects debris from a fingerprint left on a surface that can support a fluid droplet by applying ultrasonic energy directly to the droplet applied to an area with the fingerprint. The media of ultrasonic energy transfer can be water, a buffer, or an enzyme solution, however to expedite subsequent steps of DNA isolation, a buffer with a proteinase can be used.

FIG. 1 shows an image of skin debris 16 on a (fingerprint) left on a plastic surface through a light microscope at 20× magnification. The amount of skin debris varies form person to person, and print to print. The amount of skin debris left on a surface depends on skin type and finger pressure applied to the surface, and numerous other factors. Images of the debris 16 and cells 20 before and after the sonication show that substantially all of the cells 20 are removed from the plastic when using the balanced salt solution with Trypsin.

Experiment 2

DNA Sampling and Extraction from Fingerprints Left on Two Different Surface Types The purpose of these experiments was to compare the yield of DNA extracted from fingerprints left on two different common fingerprint-bearing surfaces (glass and plastic).

As illustrated in Table 1, the procedure was able to extract DNA from fingerprint samples collected on different surfaces. In these experiments two different surface types were used: polystyrene and glass. 12 volunteers participated in these experiments. Four fingerprints were collected from each volunteer. Two fingerprints from each volunteer were collected on glass surfaces, and two fingerprint samples were collected on plastic surfaces. 48 fingerprint samples were collected in total from the volunteers.

DNA was collected and extracted from all fingerprint samples using invented sampling and extraction techniques. DNA quantification (yield of DNA) was performed using a standard QuantiBlot Human Quantification Kit purchased from Applied Biosystems.

This protocol was chosen because: it detects a yield of DNA up to 0.1 ng (DNA extracted from a fingerprint contains only low concentrations of DNA); and this protocol was designed to detect only human DNA (DNA extracted from human epithelial cells may potentially contain DNA components from bacteria and yeast). The results of DNA sampling and extraction from fingerprints are presented in the Table 1.

TABLE 1

DNA yield: fingerprints on glass and plastic

| A | B<br>Dilution level for control samples in ng | C<br>Control-standard human DNA | D<br>Experiment-human DNA collected on a plastic surface | E<br>Experiment-human DNA collected on a glass surface |
|---|---|---|---|---|
| 1 | 10.000 | ● | ● | ● |
| 2 | 5.000 | ● | — | ● |
| 3 | 2.500 | ● | — | — |
| 4 | 1.250 | ● | — | — |
| 5 | 0.625 | ● | — | ● |
| 6 | 0.312 | — | — | — |
| 7 | 0.156 | — | — | — |
| 8 |  |  | ● | — |
| 9 |  |  | — | ● |

Column A identifies a row number for each sample in in columns C, D and E.

Column B represents the quantity of DNA (in nano grams) for the control samples—standard human DNA.

Column C represents the control (standard human DNA) samples. The quantity of standard DNA samples in column C is included for comparison with experimental data in columns D and E. Standard human DNA was purchased from Applies Biosystems and diluted in the quantities identified in column B.

Column D represents the yield of human DNA from fingerprint samples collected on a plastic surface.

Column E represents the yield of human DNA from fingerprint samples collected on a glass surface.

Conclusion: No significant difference in yield is found between DNA collected and extracted according to the instant method from all fingerprint samples left on a glass or a plastic surface.

Experiment 3

DNA Sampling and Extraction from Fingerprints Stored for Extended Periods of Time The purpose of these experiments was to determine the ability of this method of collecting cells and extracting DNA from cells as a function of age of the fingerprint (up to one year).

22 volunteers participated in these experiments. 4 fingerprint samples were collected from each volunteer. 88 fingerprint samples were collected in total. A first fingerprint sample from each volunteer was collected on the day of the quantification analysis. A second fingerprint sample from each volunteer was collected and stored in a closed container at room temperature for 1 month. A third fingerprint sample was collected from the volunteer and stored in a closed container at room temperature for 3 months. A fourth fingerprint sample was collected from each volunteer and stored in a closed container at room temperature for 12 months. All fingerprint samples were collected on a plastic surface (polystyrene).

Once again, the DNA quantification (yield of DNA) was performed using standard QuantiBlot Human Quantification Kit purchased from Applied Biosystems.

The results of these experiments presents on Table 2.

TABLE 2

DNA yield: fingerprint as a function of date

| A | B<br>Dilution level for control samples in ng | C<br>Control-standard human DNA | D<br>Experiment-human DNA collected the same day | E<br>Experiment-human DNA collected after 1 month of storage | F<br>Experiment-human DNA collected after 3 months of storage | G<br>Experiment-human DNA collected after 12 months of storage |
|---|---|---|---|---|---|---|
| 1 | 10.000 | ■ | ■ | ■ | ■ | ■ |
| 2 | 5.000 | ■ | ⌣ | ■ | ⌣ | ⌣ |
| 3 | 2.500 | ■ | · ⌣ | ▬ | ■ | ⌣ |
| 4 | 1.250 | ▬ | ■ | — | ⌣ | ■ |
| 5 | 0.625 | ⌣ | ■ | ● | ■ | ⌣ |
| 6 | 0.312 | (faint) | ■ | ■ | — | ⌣ |
| 7 | 0.156 | (faint) | ⌣ | ■ | (faint) | ⌣ |
| 8 | | | ■ | (faint) | ■ | ⌣ |
| 9 | | (faint) | ⌣ | · ⌣ | (faint) | ⌣ |

Table 2 shows an example of DNA yield as extracted by the invented procedure from the fingerprint samples collected the same day, after 1 month in storage, 3 months in storage, and 12 months in storage.

Column A numbers the rows of columns B-G.

Column B represents the dilution level (in nano grams) for the control samples—standard human DNA.

Column C represents the control (standard human DNA) samples. The yield of standard DNA samples in column C is included for comparison with experimental data from columns D-G. The standard human DNA was purchased from Applied Biosystems and diluted in the quantities shown in column B.

Column D shows yield of DNA from fingerprint samples collected the same day.

Column E shows yield of DNA from fingerprint samples stored at room temperature for 1 month.

Column F shows yield of DNA from fingerprint samples stored at room temperature for 3 months.

Column G shows yield of DNA from fingerprint samples stored at room temperature for 12 months.

Conclusion: No significant difference was observed in DNA yield collected and extracted from all fingerprint samples left on the plastic surface.

Experiment 4

DNA Extraction from Nail Clippings

The purpose of these experiments was to determine yield of DNA extracted from nail clippings using the new collection and extraction technique.

It is well known that human nail tissue, per se, contains no DNA, but frequently cells including skin cells, can be found on surfaces of nails and like surfaces that provide skin contact traces.

19 volunteers participated in these experiments. 2 nail samples were collected from each volunteer. 38 nail samples were collected in total. Nail samples were collected by clipping tiny pieces of nail from the volunteer using sterile scissors. The weights of the pieces of nails varied from 0.05 mg to 0.2 mg. DNA was extracted from all nail samples using the invented extraction technique.

Quantification of the yield of DNA was performed using the standard QuantiBlot Human Quantification Kit purchased from Applied Biosystems, for the above-noted reasons.

The results of these experiments are presented in Table 3.

TABLE 3

DNA yield from nail clippings

| A | B<br>Dilution level for control samples in ng | C<br>Control-standard human DNA | D<br>Experiment-human DNA extracted from nail samples | E<br>Experiment-human DNA extracted from nail samples |
|---|---|---|---|---|
| 1 | 10.000 | ■ | ■ | ■ |
| 2 | 5.000 | ■ | ■ | ■ |

TABLE 3-continued

DNA yield from nail clippings

| A | B<br>Dilution level<br>for control<br>samples<br>in ng | C<br>Control-<br>standard<br>human DNA | D<br>Experiment-<br>human DNA<br>extracted from<br>nail samples | E<br>Experiment-<br>human DNA<br>extracted from<br>nail samples |
|---|---|---|---|---|
| 3 | 2.500 | ▬ | ▬ | ▬ |
| 4 | 1.250 | ▬ | ▬ | ▬ |
| 5 | 0.625 | ⌐ | ▬ | ▬ |
| 6 | 0.312 | ⌐ | ▬ | ▬ |
| 7 | 0.156 | ⌐ | ▬ | ▬ |

Column A numbers rows of columns B-E.

Column B represents the dilution level (in nano grams) for the control samples—standard human DNA.

Column C represents the control (standard human DNA) samples. The quantity of standard DNA samples in column C is included for comparison with experimental data in columns D-E. Standard human DNA was purchased from Applied Biosystems and diluted in the quantities established in column B.

Columns D and E show the yield of DNA from nail samples.

Conclusion: Sufficient DNA can typically be extracted from small clippings of fingernail using the new extraction technique.

The method in accordance with the invention therefore permits useful quantities of human DNA to be reliably and rapidly collected from non-invasive and incidental sources such as fingerprints, human hair and nail clippings. This permits forensic scientists to work more reliably with incidental evidence that may not be conclusive using prior art methods of collection and/or analysis.

The embodiments of the invention described above are intended to be exemplary only. The scope of the invention is therefore intended to be limited solely by the scope of the appended claims.

I claim:

1. A method for collecting cells adhered to a surface for macromolecular analysis, the method comprising:
    applying a predetermined volume of an aqueous solution to the surface where the cells are adhered;
    subjecting the solution to ultrasonic waves of a frequency, power distribution and duration sufficient to detach the cells from the surface without disrupting cell membranes, thereby placing the cells in suspension in the solution, whereby the cells remain intact; and
    collecting the solution.

2. The method as claimed in claim 1 wherein the aqueous solution comprises a buffer and an agent for breaking down proteins on an outer surface of cells that bind the cells to the surface.

3. The method as claimed in claim 2 wherein the agent is Trypsin.

4. The method as claimed in claim 3 wherein the solution comprises 0.05% (w/v) Trypsin.

5. The method as claimed in claim 4 wherein between about 0.1 and 0.2 ml of the solution is applied to the surface.

6. The method as claimed in claim 1 wherein said applying the aqueous solution comprises applying the predetermined volume of the aqueous solution onto a part of a fingerprint, a footprint or a palm print.

7. The method as claimed in claim 6 wherein said applying the predetermined volume comprises applying the predetermined volume to a surface onto which the fingerprint, footprint or palm print has been transferred.

8. The method as claimed in claim 1 wherein said applying the aqueous solution comprises applying the predetermined volume of the aqueous solution onto at least a part of a hair.

9. The method as claimed in claim 1 wherein said applying the aqueous solution comprises applying the predetermined volume of the aqueous solution onto at least a part of a nail clipping.

10. The method as claimed in claim 1 wherein said applying the aqueous solution comprises applying the aqueous solution to a fingerprint, a footprint or a palm print left on the surface, or a surface onto which the fingerprint, footprint or palm print has been transferred, for an extended period of time.

11. The method as claimed in claim 10 wherein the period of time is up to at least one year.

12. The method as claimed in claim 1 wherein said subjecting comprises inserting a sonicator of an ultrasound probe into contact with the aqueous solution, and actuating the ultrasound probe to generate the ultrasonic waves.

13. The method as claimed in claim 1 wherein the frequency is between about 20 and 50 kilohertz, the power density is between about 100 to 150 Watts/centimeter squared, and the duration is between about 1 to 2 minutes.

14. The method as claimed in claim 1 further comprising a step of lysing the cells in the collected solution to recover macromolecules.

15. The method as claimed in claim 14 wherein the lysing is performed using ultrasonic waves.

16. The method as claimed in claim 15 wherein the macromolecules are DNA molecules.

17. The method as claimed in claim 16 wherein the aqueous solution comprises a buffer and an agent capable of breaking down proteins.

18. The method as claimed in claim 17 wherein the agent is Trypsin.

19. The method as claimed in claim 18 wherein the solution comprises 0.05% (w/v) Trypsin.

20. The method as claimed in claim 1 wherein the cells are present on the surface in a low density.

21. The method as claimed in claim 1 wherein the surface is selected from the group consisting of: glass, plastic, hair, nail clippings, and body-contacting surfaces.

22. The method as claimed in claim 1 wherein the cells are dead cells.

23. A method of collecting DNA from a surface for macromolecular analysis, the method comprising:
    applying a predetermined volume of an aqueous solution to the surface for collecting cells adhered to the surface;
    subjecting the aqueous solution to ultrasonic waves of a frequency, power distribution and duration sufficient to detach the cells from the surface without disrupting cell membranes, thereby placing the cells in suspension in the solution, whereby the cells remain intact;
    collecting the aqueous solution from the surface;
    lysing the collected cells in the aqueous solution; and
    isolating the DNA from debris in the aqueous solution.

24. The method as claimed in claim 23 wherein said applying a predetermined volume of aqueous solution comprises applying the aqueous solution to a part of the surface bearing a skin contact trace.

25. The method as claimed in claim 24 wherein said applying the predetermined volume of aqueous solution comprises applying the aqueous solution to a fingerprint, a footprint or a palm print.

* * * * *